US012650385B2

(12) United States Patent
Zhang et al.

(10) Patent No.: US 12,650,385 B2
(45) Date of Patent: Jun. 9, 2026

(54) METHOD AND APPARATUS FOR COLLECTING SIGNALS, TRACKING CELLS, AND IMAGING CONTROL USING A PHOTOSENSITIVE CHIP

(71) Applicant: SHANGHAI E-BLOT PHOTOELECTRIC TECHNOLOGY CO., LTD, Shanghai (CN)

(72) Inventors: Yinghao Zhang, Shanghai (CN); Zhihao Zhang, Shanghai (CN); Ketuan Zhan, Shanghai (CN); Jia Wan, Shanghai (CN)

(73) Assignee: SHANGHAI E-BLOT PHOTOELECTRIC TECHNOLOGY CO., LTD, Shanghai (CN)

( * ) Notice: Subject to any disclaimer, the term of this patent is extended or adjusted under 35 U.S.C. 154(b) by 1119 days.

(21) Appl. No.: 17/674,836

(22) Filed: Feb. 17, 2022

(65) Prior Publication Data

US 2022/0260499 A1 Aug. 18, 2022

Related U.S. Application Data

(63) Continuation-in-part of application No. 15/864,170, filed on Jan. 8, 2018, now abandoned, which is a
(Continued)

(30) Foreign Application Priority Data

Jul. 8, 2015 (CN) .......................... 201510398509.0

(51) Int. Cl.
*G01N 27/447* (2006.01)
*B25J 13/00* (2006.01)
(Continued)

(52) U.S. Cl.
CPC ............ *G01N 21/763* (2013.01); *B25J 13/00* (2013.01); *G01N 27/44717* (2013.01);
(Continued)

(58) Field of Classification Search
None
See application file for complete search history.

(56) References Cited

U.S. PATENT DOCUMENTS 5,306,468 A * 4/1994 Anderson ........ G01N 27/44717
204/612
2002/0151076 A1* 10/2002 Anderson ........ G01N 27/44782
422/63
(Continued)

FOREIGN PATENT DOCUMENTS

EP 1015872 B1 3/2005
EP 3167276 A1 5/2017
WO 2016007353 A1 1/2016

OTHER PUBLICATIONS

Yoshihiro Ohmiya, Applications of Bioluminescence Cell Based Assays and Imaging, Jan. 29, 2014 http://photobiology.info/Ohmiya. html.
(Continued)

*Primary Examiner* — Neil N Turk

(57) ABSTRACT

The present invention discloses method and apparatus for collecting signals, tracking cells, and imaging control using a photosensitive chip, wherein the method for acquiring signals by a photosensitive chip comprises: closely attaching a luminous surface of a membrane carrying a light signal to be acquired to a photosensitive chip, placing the photosensitive chip attached with the membrane carrying the light signal to be acquired in a darkroom, acquiring the light signal on the photosensitive chip in the darkroom, and performing signal processing on the acquired light signal and outputting the light signal. In the method and the
(Continued)

101
Closely attaching a luminous surface of a membrane carrying a light signal to be acquired to a photosensitive chip 102
Placing the photosensitive chip attached with the membrane carrying the light signal to be acquired in a darkroom 103
Acquiring the light signal on the photosensitive chip in the darkroom 104
Performing signal processing on the acquired light signal and outputting the light signal apparatus for acquiring signals by a photosensitive chip provided by the present invention, human participation is not needed in the whole process, the convenience and timeliness of the imaging control process are improved, and the imaging precision and efficiency are effectively improved.

9 Claims, 6 Drawing Sheets

Related U.S. Application Data continuation of application No. PCT/CN2016/084913, filed on Jun. 6, 2016.

(51) Int. Cl.
    *G01N 21/76*     (2006.01)
    *G01N 33/68*     (2006.01)
    *G06T 7/00*     (2017.01)
    *G01N 1/40*     (2006.01)
    *G01N 21/17*     (2006.01)
(52) U.S. Cl.
    CPC ... *G01N 27/44726* (2013.01); *G01N 33/6842* (2013.01); *G06T 7/0012* (2013.01); *G01N 2001/4038* (2013.01); *G01N 2021/1765* (2013.01)

(56) References Cited

U.S. PATENT DOCUMENTS

| | | | | |
|---|---|---|---|---|
| 2002/0191082 A1* | 12/2002 | Fujino | | H04N 23/70 |
| | | | | 348/E5.042 |
| 2008/0158566 A1* | 7/2008 | Suzuki | | G02B 21/361 |
| | | | | 356/450 |
| 2008/0240747 A1* | 10/2008 | Ikami | | G01N 21/6456 |
| | | | | 399/32 |
| 2009/0106851 A1 | 4/2009 | Zhuo et al. | | |
| 2014/0109560 A1* | 4/2014 | Ilievski | | B25J 9/1075 |
| | | | | 60/484 |
| 2015/0285761 A1* | 10/2015 | Pan | | G01N 27/44726 |
| | | | | 204/612 |

OTHER PUBLICATIONS

Ping-Chang Yang et al., Western blot: Technique, theory, and trouble shooting, North American Journal of Medical Sciences, vol. 4, No. 9, Sep. 2012, pp. 429-434.

Anwar M et al., A Wireless-compatible CMOS-based cellular sensor, Transducers 2009, Colorado, USA, Jun. 21-25, 2009, IEEE, Piscataway, NJ, USA, Jun. 21, 2009.

Kitchener Wilson et al., In vitro and in vivo Bioluminescence Reporter Gene Imaging of Human Embryonic Stem Cells, Journal of Visualized Experiments, No. 14, May 2, 2008.

Michela Esposito et al., Using a large area CMOS APS for direct chemiluminescence detection in Western blotting electrophoresis, Proceedings of SPIE, vol. 8317, Mar. 23, 2012, p. 831710.

M Esposito et al., CMOS APS in pre-clinical science: next generation disruptive technology for multi-modality imaging, 2012 IEEE Nuclear Science Symposiwn and Medical Imaging Conference Record (NSS/MIC), Nov. 3, 2012.

Honghao Ji et al., CMOS contact imager for monitoring cultured cells, Conference Proceedings/IEEE International Symposium on circuits and systems (ISCAS)L May 23-26, 2005, International Conference Center, Kobe, Japan, IEEE Service Center, Piscataway, NJ< May 23, 2005, pp. 3491-3494.

Jun. 3, 2024 Official summons to oral proceedings issued in European Patent Application No. 16820726.4.

Dec. 28, 2022 Indian Hearing Notice issued in Indian Patent Application No. 201817003558.

Michael A. Barry et al. (2011) "Imaging Luciferase Expressing Viruses" published in Methods in Molecular Biology, vol. 797, pp. 79-87.

Jul. 25, 2023 Notice of Reasons for Refusal issued in Japanese Patent Application No. 2022-125453.

Apr. 5, 2022 Japanese Office Action issued in Japanese Patent Application No. 2020-067922.

* cited by examiner

301

Planting cells or an animal carrying luciferase on a photosensitive chip

302

Placing the photosensitive chip planted with the cells or the animal carrying

303

Acquiring the light signal on the photosensitive chip in the darkroom

304

Performing signal processing on the acquired light signal and outputting the light signal

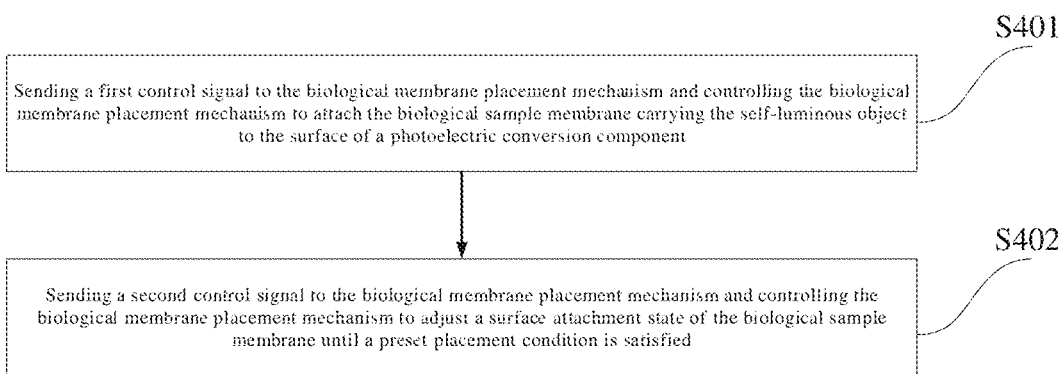

S401

Sending a first control signal to the biological membrane placement mechanism and controlling the biological membrane placement mechanism to attach the biological sample membrane carrying the self-luminous object to the surface of a photoelectric conversion component

S402

Sending a second control signal to the biological membrane placement mechanism and controlling the biological membrane placement mechanism to adjust a surface attachment state of the biological sample membrane until a preset placement condition is satisfied

Fig. 9

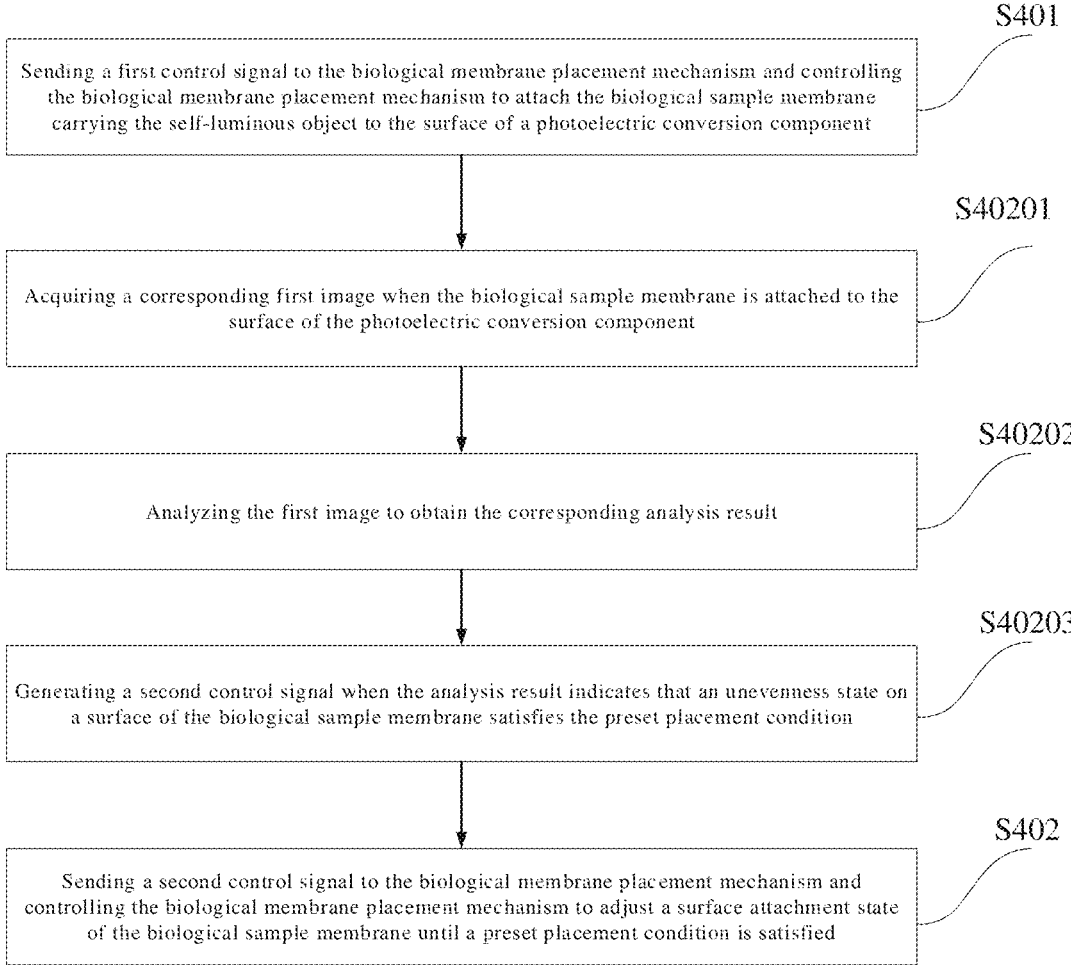

S401

Sending a first control signal to the biological membrane placement mechanism and controlling the biological membrane placement mechanism to attach the biological sample membrane carrying the self-luminous object to the surface of a photoelectric conversion component

S40201

Acquiring a corresponding first image when the biological sample membrane is attached to the surface of the photoelectric conversion component

S40202

Analyzing the first image to obtain the corresponding analysis result

S40203

Generating a second control signal when the analysis result indicates that an unevenness state on a surface of the biological sample membrane satisfies the preset placement condition

S402

Sending a second control signal to the biological membrane placement mechanism and controlling the biological membrane placement mechanism to adjust a surface attachment state of the biological sample membrane until a preset placement condition is satisfied

Fig. 10

METHOD AND APPARATUS FOR COLLECTING SIGNALS, TRACKING CELLS, AND IMAGING CONTROL USING A PHOTOSENSITIVE CHIP

TECHNICAL FIELD

The present invention relates to the technical field of signal acquisition, and in particular to methods and apparatus for method and apparatus for collecting signals, tracking cells, and imaging control using a photosensitive chip.

BACKGROUND

Western blotting is a hybridization technique that combines high-resolution gel electrophoresis with immunochemical analysis techniques. Western blotting has the advantages of large analysis capacity, high sensitivity, strong specificity and the like, and is the most commonly used method for detecting the characteristics, expression and distribution of proteins, such as qualitative and quantitative detection of tissue antigens, quality measurement of polypeptide molecules, antibody or antigen detection of viruses and the like.

The existing apparatus and methods for acquiring Western blotting signals are as follows:

Method I: a photosensitive film and an NC membrane are closely attached together, and after exposure for a certain time, development and fixation are performed, wherein the image is displayed on the film. This method has the advantages of high sensitivity and high resolution, and has the following disadvantages:

1. Large occupied space: special darkrooms (rooms), sinks, sewer pipes, etc. are required.

2. High cost: not only a developing machine and a cassette need to be purchased, but also a large amount of consumables such as photosensitive films, developing solutions, fixing solutions and the like are needed; water resource waste can be caused by washing the films.

3. Environmental pollution: washing the films requires large amounts of developing solutions and fixing solutions; meanwhile, unqualified film products are discarded. In this process, contamination with heavy metals and aromatic compounds can be caused.

4. Unstable image quality: in a darkroom, researchers cannot monitor the exposure degree in real time, and it often takes a plurality of attempts to obtain an image with a good quality. In most cases, either underexposure or overexposure occurs. Therefore, it is time-consuming and labor-consuming.

5. Time consuming: at present, digitization is a common practice for data storage, transmission and distribution, and thus, film images also need to be converted into digital images by scanning.

6. Inaccurate quantification: in most cases, an image with a good quality researchers visually determines is actually oversaturated in gray scale. Therefore, subsequent gray scale scanning is difficult to quantify accurately.

Method II: a sample is directly photographed by photosensitive equipment such as a charge-coupled apparatus (CCD). This method has the advantages that all the disadvantages of method I are overcome and has the disadvantages that the advantage of film acquisition is lost, i.e., a severe reduction in sensitivity. The reason is that all such equipment currently available on the market takes images with a CCD digital camera frame at a distance above an NC membrane. The light energy radiated by the light source can be acquired by the camera only when the light ray is within a certain small angle. More than 90% of the energy is lost. Such equipment is therefore often used for high light photography. Only individual brands claim to be useful for low-light photography of WB. But the exposure time is greatly extended compared to film. Some brands adopt a pixel merging method to sacrifice resolution to improve sensitivity which can be comparable to film. However, the image shows mosaic when being enlarged slightly, which is difficult to satisfy various requirements.

Method III: low-light signals are scanned and acquired by using CCD photosensitive units which are linearly arranged. This method has the advantages that the acquisition rate of light signals is improved and therefore the sensitivity is improved, and has the disadvantages that because the light signals are acquired by linear scanning, the whole image cannot be acquired at the same time, and therefore time difference exists in scanning of different areas; in addition, because the light source is attenuated continuously along with time, the signal intensity acquired at different time points is not comparable. Therefore, it makes many control tests incomparable.

Therefore, one technical problem that needs to be urgently solved by those skilled in the art is how to creatively provide an effective measure to solve the problems in the prior art and satisfy more requirements in practical application.

Currently, two types of biological self-luminescence detection technologies are commonly used, one is a photosensitive film technology, and the other is a camera shooting technology.

Wherein, the photosensitive film technology is similar to a conventional photographic film developing method, in a darkroom, a self-luminous object (attached to a biological sample membrane) is closely attached to a photosensitive film, and then the photosensitive film is re-developed by using a developing solution, thereby obtaining an image corresponding to the self-luminous object; however, this imaging method has the disadvantages of complex operation processes and more steps for digital processing. The camera shooting technology is similar to a shooting technology of a mobile phone, a camera and a self-luminous object are placed in a darkroom, digitized images can be directly stored in this method, but the camera is far away from the self-luminous object, so that the acquisition rate of light signals is low, a long time is needed for data acquisition, and the defects of low sensitivity and the like exist. In addition, the control processes of the above two imaging systems need human participation, and the defects of low processing efficiency, long time consumption, poor imaging effect and the like caused by incapability of ensuring the control precision of the whole imaging process exist.

CONTENT OF THE PRESENT INVENTION

The technical problem to be solved by the embodiment of the present invention is to provide a method for acquiring signals by a photosensitive chip and a method for tracking cells, wherein a signal to be detected is converted into a digital signal from a light signal, thereby quickly realizing quantitative analysis.

Correspondingly, the present invention further provides an apparatus for acquiring signals by a photosensitive chip and an apparatus for tracking cells which are used for ensuring the realization and the application of the above method.

In addition, the present invention further provides an imaging control apparatus and method for a biological sample membrane, so as to overcome the defects of complex operation processes, long imaging time consumption, artificial participation, low processing efficiency, and poor imaging effect and the like caused by incapability of ensuring the control precision of the whole imaging process in the imaging control scheme in the prior art.

The present invention solves the above technical problem by the following technical solutions.

The present invention provides a method for acquiring signals by a photosensitive chip, which comprises the following steps:

closely attaching a luminous surface of a membrane carrying a light signal to be acquired to a photosensitive chip;

placing the photosensitive chip attached with the membrane carrying the light signal to be acquired in a darkroom; the darkroom being not influenced by external light;

acquiring the light signal on the photosensitive chip in the darkroom; and performing signal processing on the acquired light signal and outputting the light signal.

In the present invention, the darkroom (or darkroom space) is a darkroom commonly used in the art for acquiring images, and may be an apparatus having an opening and closing function and a space capable of accommodating a photosensitive chip and a biological sample membrane, such as a housing comprising a light shielding cover and a base. When the darkroom is opened, for example, by moving the light shielding cover, a biological sample membrane can be placed therein; after the darkroom is closed, the acquisition of weak light such as chemical signals or fluorescent signals is not affected under the condition that the light source is not arranged inside the apparatus. The darkroom may also be additionally provided with a light source, such as an ultraviolet lamp or a white light lamp which is activated when needed to deliver a light source to a biological sample membrane. The weak light can be generated by chemical self-luminescence or by a luciferin substrate under the action of luciferase.

The signal processing and outputting are processed by signal processing equipment such as a computer or tablet computer or any other equipment with signal processing and observing functions as is conventional in the art, wherein the signal processing equipment and the photosensitive chip are connected by a signal transmission cable as is conventional in the art, and the photosensitive chip can be controlled (e.g., controlled by a controller as described below) to acquire or stop acquiring signals.

The computer or tablet computer is conventional in the art and has a signal processor for processing signals and a screen for observing a result of signal conversion. For example, after the light signal is acquired and processed and/or simulated by a computer, a content which can be displayed on a computer screen (i.e., a computer screen) and used for determining the strength of signals and the exposure time is generated. Other equipment with signal processing and observation functions as are conventional in the art may be constructed differently from the computer but with its signal processing and observation functions.

Preferably, acquiring the light signal on the photosensitive chip in the darkroom comprises the following steps:

acquiring the light signal;

observing exposure intensity in real time through a computer screen;

stopping exposure when the signal is accumulated to a preset intensity; and obtaining and storing an image generated by exposure.

Different from the scanning imaging in the prior art, the light signal acquisition in the present invention is completed by one-time imaging, namely, the whole imaging is realized by one-time photographing. For example, a photosensitive chip is located in a housing comprising a light shielding cover and a base, at this time, a membrane carrying a light signal to be acquired is closely attached to the photosensitive chip, the light shielding cover is then closed to enable the photosensitive chip to be located in a darkroom, followed by exposure and light signal acquisition, the exposure intensity is observed in real time through a computer screen, exposure is stopped when the signal is accumulated to a preset intensity, and an image generated by exposure is obtained and stored. The preset intensity (i.e., the exposure intensity) is a parameter known to those skilled in the art, and the exposure process can be started or ended by controlling the light signal acquisition of the photosensitive chip.

Preferably, when the signal acquired by the photosensitive chip is a Western blotting signal, the obtaining of the membrane carrying the light signal to be acquired comprises the following steps:

firstly, performing gel electrophoresis for a protein to be detected;

transferring the protein after the gel electrophoresis is completed;

transferring the protein to be detected in the gel to a polyvinylidene fluoride membrane or a nitrocellulose membrane;

sealing the transferred polyvinylidene fluoride membrane or the nitrocellulose membrane, adding a primary antibody resisting the protein to be detected for reaction, and adding a secondary antibody for HRP reaction; and performing chemiluminescence solution treatment on the reacted polyvinylidene fluoride membrane or the nitrocellulose membrane.

Preferably, the membrane comprises a nitrocellulose membrane and/or a polyvinylidene fluoride membrane.

Preferably, the photosensitive chip includes a CMOS photosensitive chip and a CCD photosensitive chip.

The present invention further provides an apparatus for acquiring signals by a photosensitive chip, which comprises:

an attachment module, used for closely attaching a luminous surface of a membrane carrying a light signal to be acquired to a photosensitive chip;

a placement module, used for placing the photosensitive chip attached with the membrane carrying the light signal to be acquired in a darkroom; the darkroom being not influenced by external light;

a signal acquisition module, used for completing light signal acquisition on the photosensitive chip in the darkroom; and a signal processing module, used for performing signal processing on the acquired light signal and outputting the light signal.

The present invention further provides a method for tracking cells by a photosensitive chip, which comprises the following steps:

planting cells or an animal carrying luciferase on a photosensitive chip;

placing the photosensitive chip planted with the cells or the animal carrying luciferase in a darkroom; the darkroom being not influenced by external light;

acquiring the light signal on the photosensitive chip in the darkroom; and performing signal processing on the acquired light signal and outputting the light signal.

Preferably, before planting the cells or the animal carrying luciferase on the photosensitive chip, the method further comprises: additionally arranging a glass layer on the photosensitive chip, and then planting the cells or the animal carrying luciferase on the glass layer on the photosensitive chip.

Preferably, the obtaining of the cells or the animal carrying luciferase comprises the following steps:

constructing a reporter gene plasmid in which a specific fragment of a target promoter is inserted in front of a luciferase expression sequence;

co-transfecting a regulatory sequence and a luciferase gene plasmid into a fertilized egg of a cell or an animal; and adding fluorescein to a cell culture medium.

The present invention further provides an apparatus for tracking cells by a photosensitive chip, which comprises:

a planting module, used for planting cells or an animal carrying luciferase on a photosensitive chip;

a placement module, used for placing the photosensitive chip planted with the cells or the animal carrying luciferase in a darkroom;

the darkroom being not influenced by external light;

a signal acquisition module, used for completing light signal acquisition on the photosensitive chip in the darkroom; and a signal processing module, used for performing signal processing on the acquired light signal and outputting the light signal.

The present invention further provides an imaging control apparatus for a biological sample membrane, which comprises a controller, an imaging device and a biological membrane placement mechanism, the imaging device and the biological membrane placement mechanism being communicatively connected to the controller;

wherein the imaging device comprises a housing and a photosensitive chip, a darkroom space is formed inside the housing, and the photosensitive chip is placed in the darkroom space;

the controller is used for sending a first control signal to the biological membrane placement mechanism and controlling the biological membrane placement mechanism to attach a biological sample membrane carrying a self-luminous object to a surface of the photosensitive chip;

the controller is further used for sending a second control signal to the biological membrane placement mechanism and controlling the biological membrane placement mechanism to adjust a surface attachment state of the biological sample membrane until a preset placement condition is satisfied.

In the solution, the biological sample membrane is automatically taken and attached to the surface of the photosensitive chip, and thus manual participation is not needed, the automation control degree is improved, and the execution efficiency and accuracy of the biological sample membrane are guaranteed; once the biological sample membrane is attached to the surface of the photosensitive chip, the biological sample membrane placement state is checked in time and the surface attachment state of the biological sample membrane is controlled in time, and in the whole adjustment process, manual participation is also not needed, the cost of labor is reduced and the placement efficiency is improved, the whole operation flow is simplified effectively, imaging control is shortened and time consumption is reduced, in-time and accurate adjustment of the attachment state of the biological sample membrane to an even and smooth state is realized, and subsequent imaging precision is ensured.

Preferably, the imaging control apparatus further comprises an image acquisition device communicatively connected to the controller;

the image acquisition device is used for acquiring a corresponding first image when the biological sample membrane is attached to the surface of the photosensitive chip and sending the first image to the controller;

the controller is used for analyzing the first image to obtain a corresponding analysis result;

the controller is further used for generating a second control signal when the analysis result indicates that an unevenness state on a surface of the biological sample membrane satisfies the preset placement condition.

In the solution, the image acquisition device is additionally arranged to acquire an image of the attached biological sample membrane in time, so as to determine whether the biological sample membrane is uneven or not in time, and control and adjust the unevenness in time once the unevenness is determined; simultaneously, the image of the attached biological sample membrane after adjustment is acquired in time, then a next adjustment operation is performed according to the analysis result corresponding to the image acquired in real time, and so on until the attachment state of the biological sample membrane reaches the even and smooth state, and in the whole adjustment process, manual participation is also not needed, the cost of labor is reduced and the placement efficiency is improved, the whole operation flow is simplified effectively, imaging control is shortened and time consumption is reduced, in-time and accurate adjustment of the attachment state of the biological sample membrane to an even and smooth state is realized, and subsequent imaging precision is ensured.

Preferably, the biological membrane placement mechanism comprises a driving member, a biological membrane taking and placing member and a biological membrane adjustment member, the biological membrane taking and placing member and the biological membrane adjustment member being electrically connected to the driving member, and the driving member being communicatively connected to the controller;

the driving member is used for controlling the biological membrane taking and placing member based on the first control signal to take the biological sample membrane and to attach the biological sample membrane to the surface of the photosensitive chip;

the driving member is further used for controlling the biological membrane adjustment member to adjust the surface attachment state of the biological sample membrane based on the second control signal.

In the solution, the driving member firstly drives the biological membrane taking and placing member to attach the biological sample membrane to the surface of the photosensitive chip, and then drives the biological membrane adjustment member to adjust the surface attachment state of the biological sample membrane; the biological sample membrane is placed and adjusted independently by different parts, thereby ensuring driving control's rationality, timeliness, accuracy and validity.

Preferably, the biological membrane adjustment member comprises a roller structure for rolling on a surface of the biological sample membrane to adjust a surface attachment state.

In the solution, bubbles on the surface are removed by the roller rolling on the surface of the biological sample membrane, so that the surface of the biological sample membrane after treatment is even and smooth, which satisfies the imaging demand and ensures the imaging quality.

Preferably, the analysis result corresponds to a plurality of uneven areas to be adjusted;

the controller is used for obtaining position information corresponding to the uneven areas, generating the second control signal according to the position information and sending the second control signal to the driving member;

the driving member is used for driving the roller structure to perform rolling adjustment on the uneven areas corresponding to the position information in the surface of the biological sample membrane by the second control signal until a preset even state is achieved.

In the solution, through the concrete analysis on different unevenness areas to be adjusted, it can make clear and determine where there are bubbles to be adjusted, where there are even and smooth areas with no need for adjustment, and then the pertinence is performed to these areas in time and accurately to ensure the adjustment efficiency on the surface of the biological sample membrane, thereby improving the imaging control's whole treatment efficiency.

Preferably, the biological membrane adjustment member comprises a vacuum pump structure, the vacuum pump structure being fixedly arranged on the housing;

the vacuum pump structure is used for vacuum pumping for a set duration to adjust the surface attachment state when the darkroom space is closed.

In the solution, a suction inlet through the vacuum pump is directly arranged on the housing in a penetrating manner to suck up air in the darkroom, so as to remove bubbles on the surface of biological sample membrane efficiently, thereby making the surface of the biological sample membrane after treatment smooth and even, satisfying the imaging demand and ensuring the imaging quality.

Preferably, the controller is used for sending a third control signal to the driving member and controlling the biological membrane taking and placing member to take the biological sample membrane attached to the surface of the photosensitive chip out of the housing.

In the solution, after the imaging result of the biological sample membrane is obtained, the driving member drives the biological membrane taking and placing member to take the biological sample membrane out of the darkroom, and in this process, manual operation is not needed, and the whole automation degree and the control efficiency of the control process are ensured.

Preferably, the imaging control apparatus comprises a driving mechanism electrically connected to the controller;

the housing comprises a light shielding cover and a base, one side of the light shielding cover being hinged with one side of the base;

the controller is used for sending a fourth control signal to the driving mechanism to drive the light shielding cover and the base to be closed or separated;

when the light shielding cover and the base are closed, the darkroom space is formed inside the housing.

In the solution, the light shielding cover of the housing is automatically closed or opened through the driving mechanism, and thus manual participation is not needed, and the whole automation degree and the control efficiency of the control process are ensured.

Preferably, the photosensitive chip is used for obtaining a plurality of second images inside the housing within a first set acquisition duration after the biological sample membrane is attached to the surface of the photosensitive chip, and sending the plurality of second images to the controller;

the controller is used for performing average value processing on the plurality of second images to obtain a target image.

In the solution, a plurality of second images are obtained and subjected to average value processing to obtain a final target image; compared with a case of acquiring one image, the precision of obtaining an imaging result is effectively improved, the imaging quality is ensured, and a scene required by imaging can be achieved.

Preferably, a plurality of biological sample membranes are attached to the photosensitive chip;

when the plurality of biological sample membranes are attached to the photosensitive chip, each sub-image in the target image corresponds to one of the biological sample membranes.

In the solution, a biological sample membrane or a plurality of biological sample membranes can be attached to one photosensitive chip, wherein self-luminous objects on the plurality of biological sample membranes have the same or different categories so as to satisfy the scene with higher imaging requirement, thereby greatly improving the practicability of the imaging control apparatus.

Preferably, one biological sample membrane correspondingly carries a plurality of self-luminous objects, each self-luminous object corresponds to one image acquisition area, and each image acquisition area is correspondingly provided with one photosensitive chip;

each sub-image in the target image corresponds to one of the image acquisition areas.

In the solution, one biological sample membrane can carry a self-luminous object or can carry various self-luminous objects to realize the imaging of the biological sample membrane carrying various self-luminous objects at the same time and to satisfy the scene with higher imaging requirement, thereby greatly improving the practicability of the imaging control apparatus.

Preferably, the imaging control apparatus further comprises image correction equipment;

the photosensitive chip is used for obtaining a first dark field image inside the housing within a second set acquisition duration when the biological sample membrane is not placed in the housing;

the photosensitive chip is further used for obtaining a second dark field image inside the housing within the second set acquisition duration after the biological sample membrane is attached to the surface of the photosensitive chip;

the image correction equipment is used for correcting the second dark field image according to the first dark field image to obtain a target image corresponding to the self-luminous object.

Preferably, a corresponding formula to the case that the image correction equipment corrects the second dark field image according to the first dark field image to obtain the target image corresponding to the self-luminous object is as follows:

$$I = I_0 - I_d$$

wherein I represents pixel data corresponding to the target image, $I_0$ represents pixel data corresponding to the second dark field image, and $I_d$ represents pixel data corresponding to the first dark field image.

Preferably, the photosensitive chip is further used for obtaining a bright field image inside the housing within the second set acquisition duration when the biological sample membrane is not placed in the housing and light source equipment in the darkroom space is opened;

the image correction equipment is further used for correcting the second dark field image according to the first dark field image and the bright field image to obtain the target image corresponding to the self-luminous object; or the photosensitive chip is further used for obtaining the corresponding bright field image within the set acquisition duration when the biological sample membrane is not placed in the housing, the housing is in an open state and an external light source provides a uniform light field;

The image correction equipment is further used for correcting the second dark field image according to the first dark field image and the bright field image to obtain the target image corresponding to the self-luminous object.

Preferably, a corresponding formula to the case that the image correction equipment corrects the second dark field image according to the first dark field image and the bright field image to obtain the target image corresponding to the self-luminous object is as follows:

$$I = \frac{I_0 - I_d}{I_f - I_d}$$

wherein I represents pixel data corresponding to the target image, $I_0$ represents pixel data corresponding to the second dark field image, $I_d$ represents pixel data corresponding to the first dark field image, and $I_f$ represents pixel data corresponding to the bright field image.

Preferably, the photosensitive chip includes a CMOS (complementary metal oxide semiconductor) chip, a CCD (charge coupled apparatus) chip or an amorphous silicon photoelectric conversion detector; and/or the biological sample membrane comprises a protein membrane, an agarose gel block, an agarose gel strip, a polyacrylamide gel block or a polyacrylamide gel strip. The protein membrane is a protein membrane conventional in the art, and may be, for example, a Western blotting (WB signal) membrane for detecting a protein sample prepared in the method of acquiring a signal by the above-described photosensitive chip.

The present invention further provides an imaging control method of a biological sample membrane, which is implemented based on the above-described imaging control apparatus for the biological sample membrane, and the imaging control method comprises:

sending a first control signal to a biological membrane placement mechanism and controlling the biological membrane placement mechanism to attach the biological sample membrane carrying the self-luminous object to a surface of the photosensitive chip; and sending a second control signal to a biological membrane placement mechanism and controlling the biological membrane placement mechanism to adjust a surface attachment state of the biological sample membrane until a preset placement condition is satisfied.

Preferably, after the step of controlling the biological membrane placement mechanism to attach the biological sample membrane carrying the self-luminous object to the surface of the photosensitive chip and before the step of sending the second control signal to the biological membrane placement mechanism, the method further comprises:

acquiring a corresponding first image when the biological sample membrane is attached to the surface of the photosensitive chip;

analyzing the first image to obtain a corresponding analysis result; and generating the second control signal when the analysis result indicates that an unevenness state on a surface of the biological sample membrane satisfies the preset placement condition.

Preferably, the imaging control apparatus comprises a driving mechanism and an imaging device, the driving mechanism and the imaging device being electrically connected to a controller, a housing in the imaging device comprises a light shielding cover and a base, and one side of the light shielding cover is hinged to one side of the base;

the imaging control method further comprises:

sending a fourth control signal to the driving mechanism to drive the light shielding cover and the base to be closed or separated; and forming a darkroom space inside the housing when the light shielding cover and the base are closed.

Preferably, after the darkroom space is formed inside the housing, the imaging control method further comprises:

obtaining a plurality of second images inside the housing within a first set acquisition duration; and performing average value processing on the plurality of second images to obtain a target image.

Preferably, when the imaging control apparatus further comprises an image correction equipment, the imaging control method further comprises:

obtaining, by the photosensitive chip, a first dark field image inside the housing within a second set acquisition duration when the biological sample membrane is not placed in the housing;

obtaining a second dark field image inside the housing within the second set acquisition duration after the biological sample membrane is attached to the surface of the photosensitive chip; and correcting, by the image correction equipment, the second dark field image according to the first dark field image to obtain the target image corresponding to the self-luminous object.

On the basis of the general knowledge in the art, the preferred conditions can be combined arbitrarily to obtain preferred embodiments of the present invention.

Compared with the prior art, the embodiments of the present invention have the following advantages:

According to the solution provided by the present invention, by closely attaching a luminous surface of a membrane carrying a light signal to be acquired to a photosensitive chip, the photosensitive chip attached with the membrane carrying the light signal to be acquired is placed in a darkroom, the photosensitive chip acquires the light signal in the darkroom, and the acquired light signal is subjected to signal processing and then output. The direct contact photosensitive chip completes signal acquisition, can acquire the whole image simultaneously, and avoids light signal loss to the utmost extent, thereby improving the sensitivity and not reducing the resolution. This not only preserves all the advantages of the three methods in the background, but also avoids their respective disadvantages.

In addition, through the arrangement of biological membrane placement mechanism, the biological sample membrane can be automatically taken and placed to the surface of the photosensitive chip (or named photoelectric conversion component) in the darkroom, and the surface attachment state of the biological sample membrane can be adjusted in time, for example, the surface attachment state of the biological sample membrane needs to be adjusted to an even and smooth state in time when the surface is uneven due to bubbles thereon, and in the whole process, manual participation is not needed, input cost of labor is reduced, the convenience and the timeliness realized in the imaging control process are improved, the imaging quality and effect on the biological sample membrane are improved when the timeliness, precision and efficiency in the imaging control of the biological sample membrane are ensured, and the application scene with higher imaging requirement is satisfied.

BRIEF DESCRIPTION OF THE DRAWINGS

In order to more clearly illustrate the technical solutions in the embodiments of the present invention or in the prior art, the drawings required to be used in the description of the embodiments or the prior art are briefly introduced below. It is obvious that the drawings in the description below are some embodiments of the present invention, and it is obvious for those skilled in the art that other drawings can be obtained according to the drawings without creative efforts.

FIG. 9 is a flow chart of an imaging control method for a biological sample membrane according to the present invention.

FIG. 10 is a flow chart of an imaging control method for a biological sample membrane according to the present invention.

DETAILED DESCRIPTION OF THE PREFERRED EMBODIMENT

In order to make the objectives, technical solutions and advantages of the embodiments of the present invention clearer, the technical solutions in the embodiments of the present invention will be clearly and completely described below with reference to the drawings in the embodiments of the present invention, and it is obvious that the described embodiments are some embodiments of the present invention, but not all the embodiments of the present invention. Based on the embodiments of the present invention, all other embodiments obtained by those of ordinary skill in the art without creative efforts shall fall within the protection scope of the present invention.

Embodiment 1

A method for acquiring signals by a photosensitive chip provided in the embodiment of the present invention is described below in detail.

Figure 1:
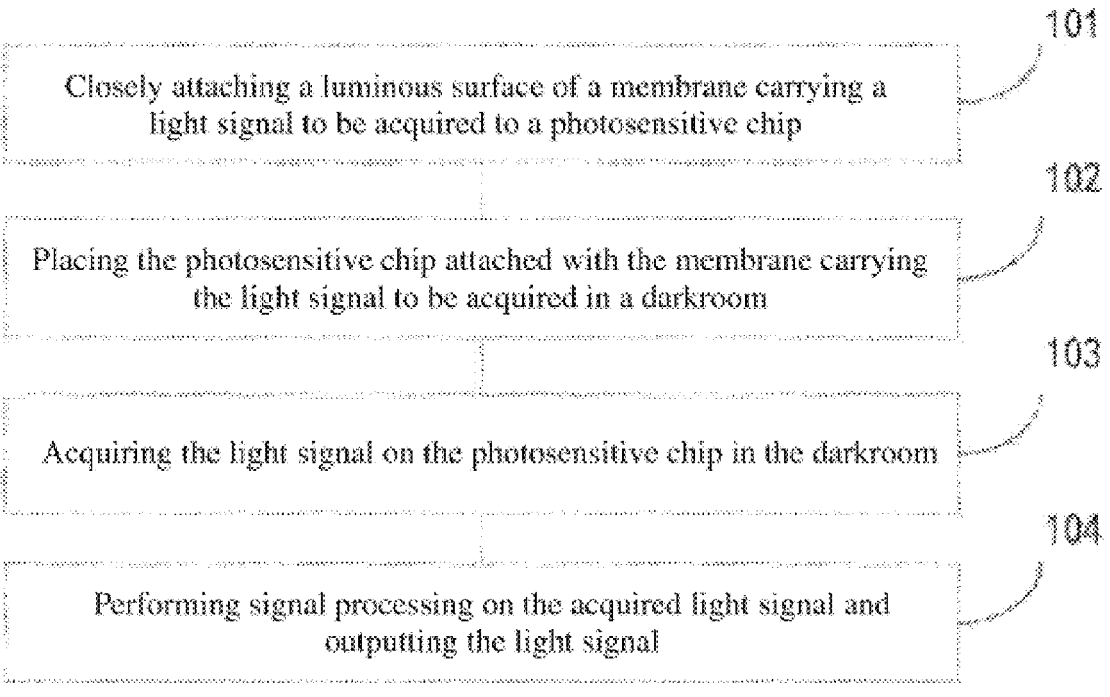
FIG. 1 is a schematic flow chart of a method for acquiring signals by a photosensitive chip according to the present invention.

Referring to FIG. 1, a schematic flow chart of a method for acquiring signals by a photosensitive chip according to the present invention is shown, and the method may specifically comprise the following steps:

Step 101, closely attaching a luminous surface of a membrane carrying a light signal to be acquired to a photosensitive chip;

in practical application, when a photosensitive chip is adopted to acquire a Western blotting signal, the obtaining of the membrane carrying the light signal to be acquired comprises the following steps:

firstly, performing gel electrophoresis for a protein to be detected;

transferring the protein after the gel electrophoresis is completed;

transferring the protein to be detected in the gel to a polyvinylidene fluoride membrane or a nitrocellulose membrane;

sealing the transferred polyvinylidene fluoride membrane or the nitrocellulose membrane, adding a primary antibody resisting the protein to be detected for reaction, and adding a secondary antibody for HRP reaction; and performing chemiluminescence solution treatment on the reacted polyvinylidene fluoride membrane or the nitrocellulose membrane.

In application, the membranes used mainly include nitrocellulose membranes (NC membranes) and/or polyvinylidene fluoride membranes (PVDF membranes). The photosensitive chip used includes a CMOS photosensitive chip, a CCD photosensitive chip and the like. Considering that the manufacturing cost of the photosensitive chip with a larger size is high, in practice, if the chip splicing technology is utilized to achieve a better effect, the cost will be greatly reduced, so that the photosensitive chip can also be an array of a CMOS photosensitive chip or a CCD photosensitive chip.

Step 102, placing the photosensitive chip attached with the membrane carrying the light signal to be acquired in a darkroom; the darkroom being not influenced by external light;

in order not to be influenced by external light, the photosensitive chip attached with the membrane carrying the light signal to be acquired needs to be placed in a dark environment, and the implementation mode can be selected according to specific environment, the implementation is easy to realized, and a light shielding cover can be buckled for the photosensitive chip.

Step 103, acquiring the light signal on the photosensitive chip in the darkroom;

in practical application, acquiring the light signal on the photosensitive chip in the darkroom comprises the following steps:

acquiring the light signal;

observing exposure intensity in real time through a computer screen;

stopping exposure when the signal is accumulated to a preset intensity; and obtaining and storing an image generated by exposure.

Step 104, performing signal processing on the acquired light signal and outputting the light signal.

In application, a processor such as a single chip, an FPGA and a CPU can be adopted to perform signal processing on the acquired light signal and output the light signal. The signal processing method is mature at present, and the signal processing in the present solution can be completed, so that the detailed description is omitted here.

The following description of the acquisition of a Western blotting (WB signal) membrane by the photosensitive chip is described in detail with reference to practical applications:

The working principle of Western blotting is as follows:

1. A cell or tissue extract was separated longitudinally on a polypropylene gel using an electric field (see left, bottom for flow chart for this step).

2. Protein bands were transferred transversely onto a nitrocellulose membrane (NC membrane) using an electric field, wherein relative positions of the bands were not changed and are called as Blot.

3. Sealing: the blotted membrane was soaked in bovine serum albumin (BSA) solution; BSA was allowed to occupy unoccupied areas of the protein bands; and subsequent antibodies were prevented from being adsorbed by these areas, so that the antibodies could only specifically bind to antigens thereof.

4. Antibody incubation: the antibodies were previously hinged with horseradish peroxidase (HRP); the antibodies and the NC membrane were incubated by soaking together; and the antibodies specifically bound to the antigens thereof.

5. Signal acquisition: the NC membrane was soaked in an HRP substrate-containing solution; HRP catalyzed substrates thereof to releases their fluorescence; and a fluorescent signal was acquired using a photosensitive film or an electronic photosensitive system.

The steps before WB light signal acquisition were as follows:

(1) protein sample acquisition: after bacteria induction expression, cells could be directly lysed by an electrophoresis loading buffer, and then eukaryotic cells were added with a homogenized buffer for mechanical homogenization or ultrasonic homogenization for 0.5 to 1 min at room temperature; then the reaction solution was centrifuged at 13,000 g for 15 min at 4° C.; and the supernatant was taken as a sample;

(2) electrophoresis: an electrophoresis gel was prepared for SDS-PAGE;

(3) transfer: 1) after the electrophoresis was completed, gel strips were cut to a suitable size, equilibrated with a membrane transfer buffer, and run for 5 min×3 times; 2) membrane treatment: filter paper and an NC membrane with the same size as the gel strips were cut in advance and soaked in a membrane transfer buffer for 10 min; and 3) membrane transfer: an anode carbon plate, a 24-layer filter paper, an NC membrane, a gel, a 24-layer filter paper and a cathode carbon plate were placed from bottom to top in sequence on a membrane transfer apparatus, the filter paper, the gel and the NC membrane were accurately aligned, bubbles were removed in each step, a heavy object with a weight of 500 g was pressed upwards, and the redundant solution on the carbon plates was sucked to be dry; a power supply was switched on with a constant current of 1 mA/cm$^2$, followed by transferring for 1.5 hrs; after the transfer was completed, the power supply was cut off to take out the membrane, and membrane strips to be detected were cut for Western blotting; and the strips with a protein standard were dyed, placed into a membrane dyeing solution for 50 s, decolorized for many times in 50% methanol until the background became clear, then washed with double distilled water, air-dried, stored in two layers of filter paper, and then compared with a color development result; and (4) immune reaction: the membrane was washed with 0.01 M PBST for 5 min×3 times;

a blocking solution was added, and the mixture was shaken steadily at room temperature for 1 hr;

the coating solution was removed, and the resulting membrane was washed with 0.01 M PBST for 5 min×3 times;

a primary antibody (diluted with 0.01 M PBS at an appropriate dilution ratio, wherein the solution must cover the whole membrane) was added, and incubated at 4° C. for 12 hrs or above; the negative control group was added with 1% BSA instead of the primary antibody, and the rest of steps were the same as those of the experimental group;

the primary antibody and 1% BSA were removed, and the resulting membrane was washed with 0.01 M PBS for 5 min×4 times;

a horseradish peroxidase-conjugated secondary antibody (diluted with 0.01 M PBST at an appropriate dilution ratio) was added and shaken steadily at room temperature for 2 hrs;

the secondary antibody was removed, and the resulting membrane was washed with 0.01 M PBST for 5 min×4 times; and the membrane was treated with a chemiluminescence solution, and HRP met and catalyzed a chemical substrate in the solution to emit its fluorescence.

A fluorescence signal was acquired by using a method for directly attaching a digital photosensitive chip to a membrane:

the membrane soaked in the chemiluminescent solution was taken out, the redundant solution was removed with absorbent paper, and then a luminous surface of the membrane was attached to the digital photosensitive chip;

the membrane was pressed using an even object to ensure that the membrane was directly and closely attached to the digital photosensitive chip;

a cover is buckled, so that the digital photosensitive chip and the membrane were in a dark environment, thereby avoiding the external light pollution;

the photosensitive chip was controlled by a computer to start acquiring chemiluminescence signals; the exposure degree was observed in real time through a computer screen, and the exposure was stopped when the signals were accumulated to proper intensity; and an image generated by the exposures was obtained and stored, which could be used for quantitative and qualitative analysis.

In this embodiment, signals were acquired with the help of the contact photosensitive chip, and in this process, a light signal was converted into a digital signal, thereby completing the quantitative analysis.

Embodiment 2

An apparatus for acquiring signals by a photosensitive chip provided in the embodiment of the present invention is described below in detail.

Figure 2:
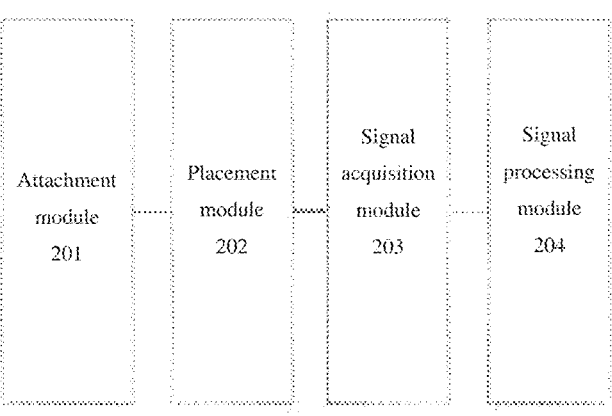
FIG. 2 is a schematic structural diagram of an apparatus for acquiring signals by a photosensitive chip according to the present invention.

Referring to FIG. 2, a schematic structural diagram of an apparatus for acquiring signals by a photosensitive chip according to the present invention is shown, and the apparatus specifically comprises:

an attachment module 201, used for closely attaching a luminous surface of a membrane carrying a light signal to be acquired to a photosensitive chip;

a placement module 202, used for placing the photosensitive chip attached with the membrane carrying the light signal to be acquired in a darkroom; the darkroom being not influenced by external light;

a signal acquisition module 203, used for completing light signal acquisition on the photosensitive chip in the darkroom; and a signal processing module 204, used for performing signal processing on the acquired light signal and outputting the light signal.

For the apparatus embodiment, since it is substantially similar to the method embodiment, the description is relatively simple, and reference may be made to the partial description of the method embodiment for relevant points.

Embodiment 3

A method for tracking cells by a photosensitive chip provided in the embodiment of the present invention is described below in detail.

Figure 3:
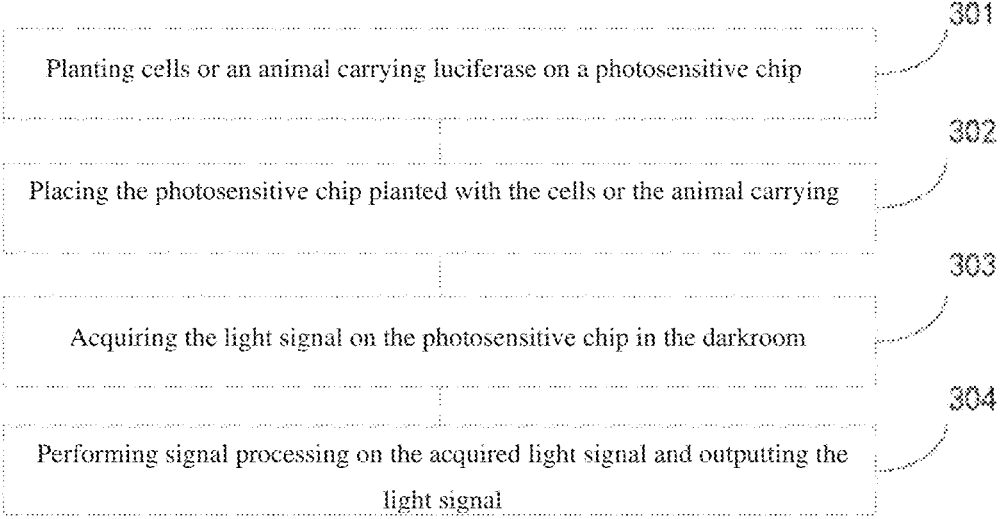
FIG. 3 is a schematic flow chart of a method for tracking cells by a photosensitive chip according to the present invention.

Referring to FIG. 3, a method for tracking cells by a photosensitive chip according to the present invention is shown, which may specifically comprise:

Step 301, planting cells or an animal carrying luciferase on a photosensitive chip;

the photosensitive chip is usually covered with a transparent protective layer, or a glass layer or a resin layer or other materials, a thickness of the protective layer being usually less than 0.5 mm.

In practice, considering the tracking effect and the secondary use of the photosensitive chip, a glass layer can be additionally arranged on the photosensitive chip before the cells or the animal carrying luciferase are planted on the photosensitive chip, and then the cells or the animal carrying luciferase are planted on the glass layer of the photosensitive chip, so that the cleaning in the later period is more convenient.

For an instrument using a photosensitive chip without a luminous module, it is generally tried to make cells or small animals (such as nematodes and fruit flies) have self-luminescence capability, and it is a common method to transfer a luciferase gene to make cells or animals and plants have self-luminescence capability.

Luciferase is a protein produced at the tail of firefly, and can catalyze luciferin to react with oxygen in the presence of ATP to emit fluorescence. The gene of luciferase and DNA sequence for regulating transcription are transferred into cells or animals and plants together by means of bioengineering method and integrated on host chromosome. The protein molecules expressed by the host, which have special structures and function of regulating gene expression, are specifically combined with the DNA sequence for regulating transcription, thereby enhancing the expression of luciferase genes.

The obtaining of the luciferase-carrying cells or animal comprises the following steps:

constructing a reporter gene plasmid in which a specific fragment of a target promoter is inserted in front of a luciferase expression sequence, specifically for example pGL3-basic;

co-transfecting a regulatory sequence and a luciferase gene plasmid into a fertilized egg of a cell or an animal (transgenic animal); and adding luciferin into a cell culture medium, and catalyzing, by luciferase, luciferin to react with oxygen by using energy provided by ATP in cells to generate fluorescence. In this way, the instrument can track the migration trajectory of the cells or the animal. This method can be used in animal behavior experiment.

Step 302, placing the photosensitive chip planted with the cells or the animal carrying luciferase in a darkroom; the darkroom being not influenced by external light;

Step 303, acquiring the light signal on the photosensitive chip in the darkroom; and Step 304, performing signal processing on the acquired light signal and outputting the light signal.

Embodiment 4

An apparatus for tracking cells by a photosensitive chip provided in the embodiment of the present invention is described below in detail.

Figure 4:
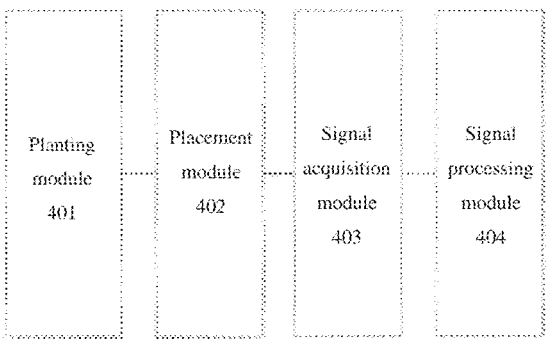
FIG. 4 is a schematic structural diagram of an apparatus for tracking cells by a photosensitive chip according to the present invention.

Referring to FIG. 4, a schematic structural diagram of an apparatus for tracking cells by a photosensitive chip according to the present invention is shown, and the apparatus specifically comprises:

a planting module 401, used for planting cells or an animal carrying luciferase on a photosensitive chip;

a placement module 402, used for placing the photosensitive chip planted with the cells or the animal carrying luciferase in a darkroom; the darkroom being not influenced by external light;

a signal acquisition module 403, used for completing light signal acquisition on the photosensitive chip in the darkroom; and a signal processing module 404, used for performing signal processing on the acquired light signal and outputting the light signal.

The solution of the present invention can be widely applied to the acquisition of a Western blotting signal, the monitoring and comparison of low-light intensity in a liquid drop array, the observation of cell migration and division by planting cells on a photosensitive chip, or the dynamic process of certain molecular expression and the like.

It should be noted that, for simplicity of description, the method embodiments are shown as a series of combinations of acts, but those skilled in the art will recognize that the embodiments of the present invention are not limited by the order of acts, as some steps may occur in other orders or concurrently in accordance with the embodiments of the present invention. Secondly, those skilled in the art will appreciate that the embodiments described in the specification belong to preferred embodiments and that no particular act is required to implement the embodiments of the present invention.

For the apparatus embodiment, since it is substantially similar to the method embodiment, the description is relatively simple, and reference may be made to the partial description of the method embodiment for relevant points.

The embodiments in the specification are all described in a progressive manner, and each embodiment focuses on differences from other embodiments, and portions that are the same and similar between the embodiments may be referred to each other.

Embodiment 5

Figure 5:
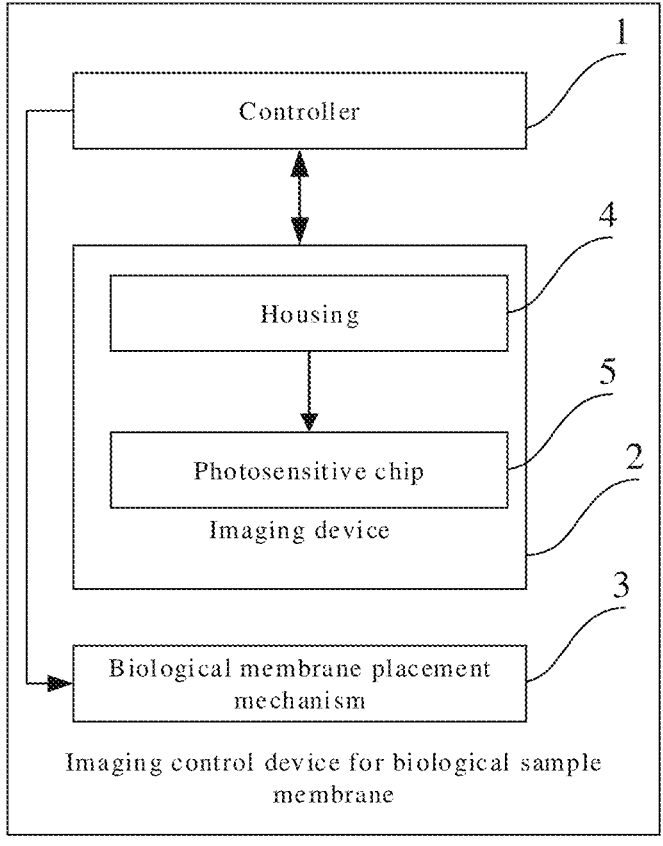
FIG. 5 is a schematic diagram of a first structure of an imaging control apparatus for a biological sample membrane according to the present invention.

As shown in FIG. 5, an imaging control apparatus for a biological sample membrane according to this embodiment comprises a controller 1, and an imaging device 2 and a biological membrane placement mechanism 3 communicatively connected to the controller 1.

Wherein the imaging device 2 comprises a housing 4 and a photosensitive chip 5, a darkroom space is formed inside the housing 4, and the photosensitive chip 5 is placed in the darkroom space.

Figure 6:
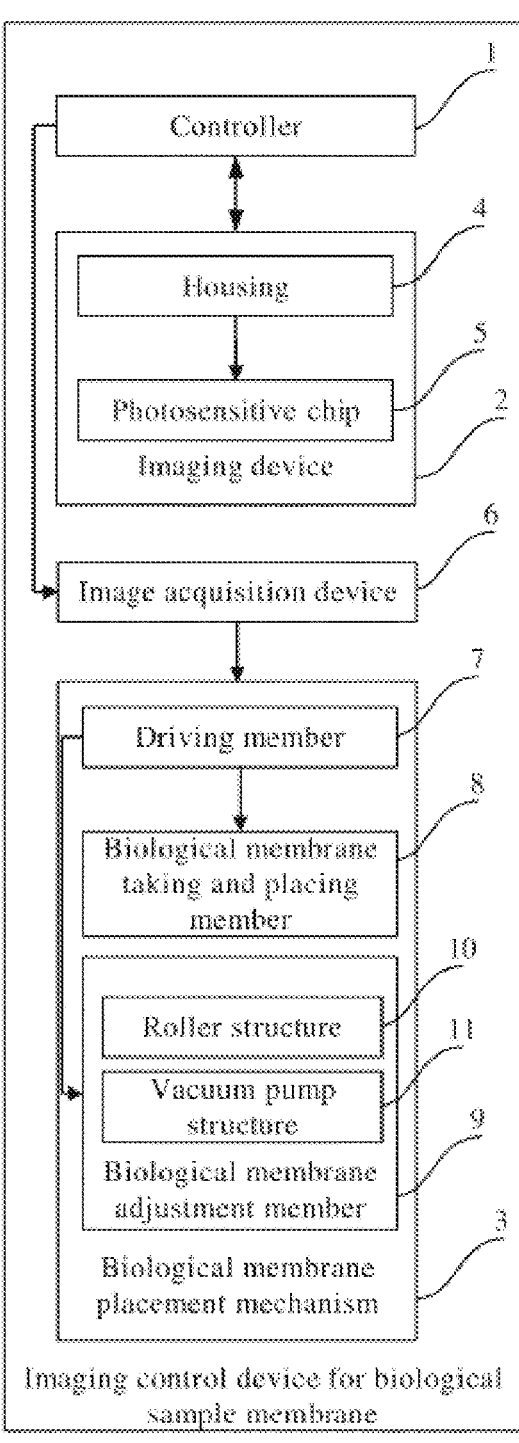
FIG. 6 is a schematic diagram of a second structure of an imaging control apparatus for a biological sample membrane according to the present invention.

Specifically, as shown in FIG. 6, the housing 4 comprises a light shielding cover A and a base B, wherein one side of the light shielding cover A is hinged with one side of the base B, and at this time, the light shielding cover A is in an open state, and a darkroom space is not formed inside the housing 4.

Figure 7:
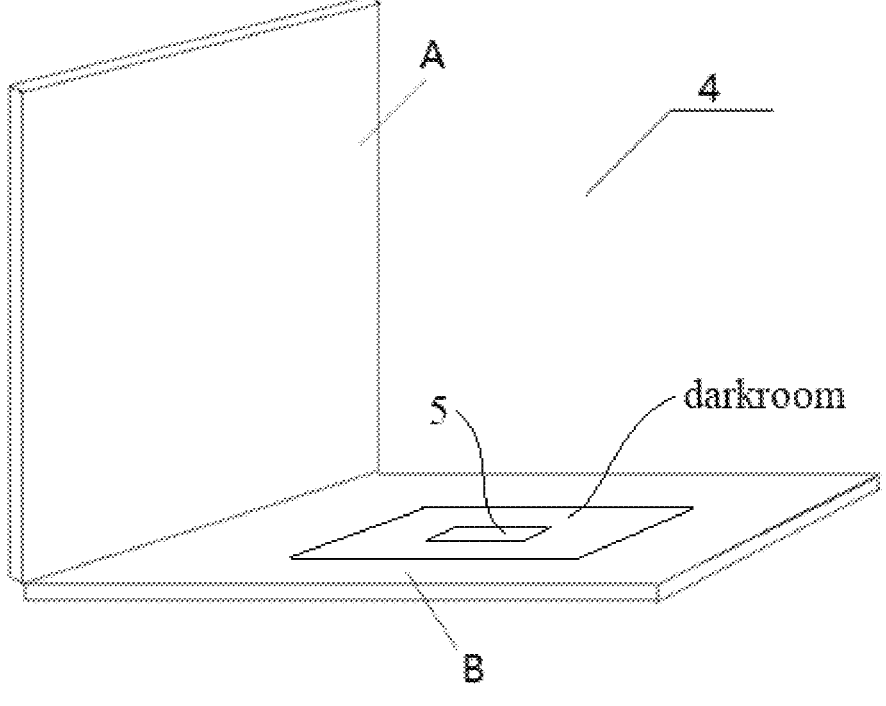
FIG. 7 is a schematic structural diagram of a housing in an open state according to the present invention.

As shown in FIG. 7, when the light shielding cover A and the base B are closed, the darkroom space is formed inside the housing 4 to ensure effective acquisition of a weak signal corresponding to a self-luminous object carried on the biological sample membrane.

The controller 1 is used for sending a first control signal to the biological membrane placement mechanism 3 and controlling the biological membrane placement mechanism 3 to attach a biological sample membrane carrying a self-luminous object to a surface of the photosensitive chip 5;

the controller 1 is further used for sending a second control signal to the biological membrane placement mechanism 3 and controlling the biological membrane placement mechanism 3 to adjust a surface attachment state of the biological sample membrane until a preset placement condition is satisfied.

In the solution, the biological sample membrane is automatically taken and attached to the surface of the photosensitive chip, and thus manual participation is not needed, the automation control degree is improved, and the execution efficiency and accuracy of the biological sample membrane are guaranteed; once the biological sample membrane is attached to the surface of the photosensitive chip, the biological sample membrane placement state is checked in time and the surface attachment state of the biological sample membrane is controlled in time, and in the whole adjustment process, manual participation is also not needed, the cost of labor is reduced and the placement efficiency is improved, the whole operation flow is simplified effectively, imaging control is shortened and time consumption is reduced, in-time and accurate adjustment of the attachment state of the biological sample membrane to an even and smooth state is realized, and subsequent imaging precision is ensured.

The imaging control apparatus for the biological sample membrane can be manually operated to open or close through the arrangement of physical keys or touch keys or by means of voice remote control (such as by presetting wake-up keywords "**, open imaging control") and other manners, and which manner is specifically adopted can be determined or adjusted according to actual scene requirements, and the details are not repeated here.

The biological membrane placement mechanism 3 may be a mechanical gripper, the specific shape design may be flexibly adjusted according to the shape, size and the like of the biological sample membrane, so long as the operation such as taking and placing a biological sample membrane can be realized.

The photosensitive chip 5 comprises a CMOS chip, a CCD chip, or an amorphous silicon photoelectric conversion detector and the like.

The biological sample membrane comprises a protein membrane, an agarose gel block, an agarose gel strip, a polyacrylamide gel block or a polyacrylamide gel strip and the like. The protein membrane is a protein membrane conventional in the art, and may be, for example, a Western blotting (WB signal) membrane of a protein sample prepared by the method of Embodiment 1.

In this embodiment, through the arrangement of biological membrane placement mechanism, the biological sample membrane can be automatically taken and placed to the surface of the photosensitive chip (or named photoelectric conversion component) in the darkroom, and the surface attachment state of the biological sample membrane can be adjusted in time, for example, the surface attachment state of the biological sample membrane needs to be adjusted to an even and smooth state in time when the surface is uneven due to bubbles thereon, and in the whole process, manual participation is not needed, input cost of labor is reduced, the convenience and the timeliness realized in the imaging control process are improved, the imaging quality and effect on the biological sample membrane are improved when the timeliness, precision and efficiency in the imaging control of the biological sample membrane are ensured, and the application scene with higher imaging requirement is satisfied.

Embodiment 6

Figure 8:
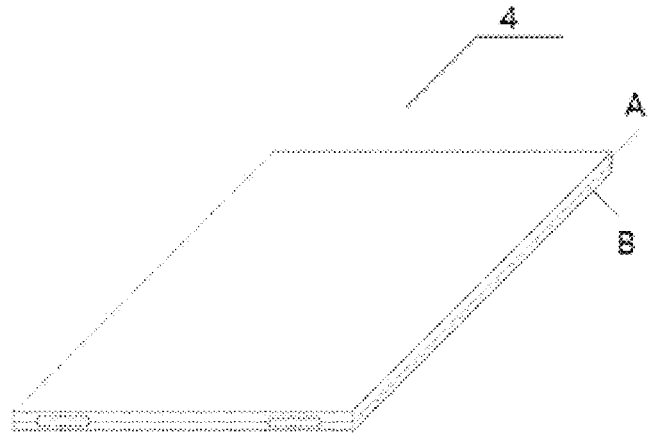
FIG. 8 is a schematic structural diagram of a housing in a closed state_according to the present invention.

As shown in FIG. 8, an imaging control apparatus for a biological sample membrane according to the embodiment is a further improvement of Embodiment 5, and the improvement is specifically as follows:

In an implementable solution, the imaging control apparatus further comprises an image acquisition device 6 communicatively connected to the controller 1; the image acquisition device 6 is used for acquiring a corresponding first image when the biological sample membrane is attached to the surface of the photosensitive chip 5 and sending the first image to the controller 1;

the controller 1 is used for analyzing the first image to obtain a corresponding analysis result;

the controller 1 is further used for generating a second control signal when the analysis result indicates that an unevenness state on a surface of the biological sample membrane satisfies the preset placement condition.

In the solution, the image acquisition device 6 is additionally arranged to acquire an image of the attached biological sample membrane in time, so as to determine whether the biological sample membrane is uneven or not in time, and control and adjust the unevenness in time once the unevenness is determined; simultaneously, the image of the attached biological sample membrane after adjustment is acquired in time, then a next adjustment operation is performed according to the analysis result corresponding to the image acquired in real time, and so on until the attachment state of the biological sample membrane reaches the even and smooth state, and in the whole adjustment process, manual participation is also not needed, the cost of labor is reduced and the placement efficiency is improved, the whole operation flow is simplified effectively, imaging control is shortened and time consumption is reduced, in-time and accurate adjustment of the attachment state of the biological sample membrane to an even and smooth state is realized, and subsequent imaging precision is ensured.

Wherein the image acquisition device 6 comprises, but is not limited to, one or more cameras. When the image acquisition device 6 comprises a plurality of cameras, each camera respectively obtains one or more first images and sends the first images to the controller 1, and the controller 1 respectively analyzes and processes the first images to obtain a final analysis result. Compared with a case of acquiring one image, the precision of obtaining the analysis result is effectively improved, and thus the surface of the biological sample membrane is adjusted in time and effectively, thereby ensuring the imaging quality.

In an implementable solution, the biological membrane placement mechanism 3 comprises a driving member 7, a biological membrane taking and placing member 8 and a biological membrane adjustment member 9, the biological membrane taking and placing member and the biological membrane adjustment member being electrically connected to the driving member 7, and the driving member 7 being communicatively connected to the controller 1;

the driving member 7 is used for controlling the biological membrane taking and placing member 8 to based on the first control signal take the biological sample membrane and to attach the biological sample membrane to the surface of the photosensitive chip 5;

the driving member 7 is further used for controlling the biological membrane adjustment member 9 to adjust the surface attachment state of the biological sample membrane based on the second control signal.

In the solution, the driving member 7 firstly drives the biological membrane taking and placing member 8 to attach the biological sample membrane to the surface of the photosensitive chip 5, and then drives the biological membrane adjustment member 9 to adjust the surface attachment state of the biological sample membrane; the biological sample membrane is placed and adjusted independently by different parts, thereby ensuring driving control's rationality, timeliness, accuracy and validity.

In addition, the controller 1 is used for sending a third control signal to the driving member 7 to control the biological membrane taking and placing member 8 to take the biological sample membrane attached to the surface of the photosensitive chip 5 out of the housing 4.

In the solution, after the imaging result of the biological sample membrane is obtained, the driving member 7 drives the biological membrane taking and placing member 8 to take the biological sample membrane out of the darkroom, and in this process, manual operation is not needed, and the whole automation degree and the control efficiency of the control process are ensured.

In an implementable solution, the biological membrane adjustment member 9 comprises a roller structure 10 for rolling on a surface of the biological sample membrane to adjust a surface attachment state.

In the solution, bubbles on the surface are removed by the roller rolling on the surface of the biological sample membrane, so that the surface of the biological sample membrane after treatment is even and smooth, which satisfies the imaging demand and ensures the imaging quality.

Specifically, the analysis result corresponds to a plurality of uneven areas to be adjusted;

the controller 1 is used for obtaining position information corresponding to the uneven areas, generating a second control signal according to the position information and sending the second control signal to the driving member 7;

the driving member 7 is used for driving the roller structure 10 to perform rolling adjustment on the uneven area corresponding to the position information in the surface of the biological sample membrane by the second control signal until a preset even state is achieved.

In the solution, through the concrete analysis on different unevenness areas to be adjusted, it can make clear and determine where there are bubbles to be adjusted, where there are even and smooth areas with no need for adjustment, and then the pertinence is performed to these areas in time and accurately to ensure the adjustment efficiency on the surface of the biological sample membrane, thereby improving the imaging control's whole treatment efficiency.

The adjustment sequence of the plurality of uneven areas to be adjusted can generate an optimized adjustment path based on the distance between the plurality of uneven areas to be adjusted, so that these areas can be adjusted in sequence according to the optimized adjustment path or adjusted directly and randomly until the adjustment of all the areas is completed; or these areas are adjusted in sequence from top to bottom and from left to right until the adjustment of all the areas is completed, and the like, wherein the specific manner can be determined or adjusted according to the actual situation.

In an implementable solution, the biological membrane adjustment member 9 comprises a vacuum pump structure 11, the vacuum pump structure 11 being fixedly arranged on the housing 4;

the vacuum pump structure 11 is used for vacuum pumping for a set duration to adjust the surface attachment state when the darkroom space is closed.

In the solution, a suction inlet through the vacuum pump is directly arranged on the housing 4 in a penetrating manner to suck up air in the darkroom, so as to remove bubbles on the surface of biological sample membrane efficiently, thereby making the surface of the biological sample membrane after treatment smooth and even, satisfying the imaging demand and ensuring the imaging quality. In an implementable solution, the imaging control apparatus comprises a driving mechanism electrically connected to the controller 1;

the controller 1 is used for sending a fourth control signal to the driving mechanism 12 to drive the light shielding cover A and the base B of the housing 4 to be closed or separated.

In the solution, the light shielding cover A of the housing 4 is automatically closed or opened through the driving mechanism 12, and thus manual participation is not needed, and the whole automation degree and the control efficiency of the control process are ensured. In an implementable solution, the photosensitive chip 5 is used for obtaining a plurality of second images inside the housing 4 within a first set acquisition duration after the biological sample membrane is attached to the surface of the photosensitive chip 5, and sending the plurality of second images to the controller 1;

the controller 1 is used for performing average value processing on the plurality of second images to obtain a target image.

In the solution, a plurality of second images are obtained and subjected to average value processing to obtain a final target image; compared with a case of acquiring one image, the precision of obtaining an imaging result is effectively improved, the imaging quality is ensured, and a scene required by imaging can be achieved.

In an implementable solution, a plurality of biological sample membranes are attached to the photosensitive chip 5;

when the plurality of biological sample membranes are attached to the photosensitive chip 5, each sub-image in the target image corresponds to one of the biological sample membranes.

In the solution, a biological sample membrane or a plurality of biological sample membranes can be attached to one photosensitive chip 5, wherein self-luminous objects on the plurality of biological sample membranes have the same or different categories so as to satisfy the scene with higher imaging requirement, thereby greatly improving the practicability of the imaging control apparatus.

In an implementable solution, one biological sample membrane correspondingly carries a plurality of self-luminous objects, each self-luminous object corresponds to one image acquisition area, and each image acquisition area is correspondingly provided with one photosensitive chip 5;

each sub-image in the target image corresponds to one image acquisition area.

In an implementable solution, the imaging control apparatus further comprises image correction equipment;

the photosensitive chip is used for obtaining a first dark field image inside the housing within a second set acquisition duration when the biological sample membrane is not placed in the housing;

the photosensitive chip is further used for obtaining a second dark field image inside the housing within the second set acquisition duration after the biological sample membrane is attached to the surface of the photosensitive chip;

the image correction equipment is used for correcting the second dark field image according to the first dark field image to obtain the target image corresponding to the self-luminous object.

Specifically, a corresponding formula to the case that the image correction equipment corrects the second dark field image according to the first dark field image to obtain a target image corresponding to the self-luminous object is as follows:

$$I = I_0 - I_d$$

wherein I represents pixel data corresponding to the target image, $I_0$ represents pixel data corresponding to the second dark field image, and $I_d$ represents pixel data corresponding to the first dark field image.

The photosensitive chip is further used for obtaining a bright field image inside the housing within the second set acquisition duration after the biological sample membrane is not placed in the housing and light source equipment in the darkroom space is opened;

the image correction equipment is used for correcting the second dark field image according to the first dark field image and the bright field image to obtain the target image corresponding to the self-luminous object; or the photosensitive chip is further used for obtaining the corresponding bright field image within the set acquisition duration when the biological sample membrane is not placed in the housing, the housing is in an open state and an external light source provides a uniform light field;

specifically, a corresponding formula to the case that the image correction equipment corrects the second dark field image according to the first dark field image and the bright field image to obtain the target image corresponding to the self-luminous object is as follows:

$$I = \frac{I_0 - I_d}{I_f - I_d}$$

wherein I represents pixel data corresponding to the target image, $I_0$ represents pixel data corresponding to the second dark field image, $I_d$ represents pixel data corresponding to the first dark field image, and $I_f$ represents pixel data corresponding to the bright field image.

In the solution, the target image of the self-luminous object with higher definition can be effectively and more accurately obtained, and in this process, the operation process is simple, time consumption for imaging is short, and the imaging control apparatus also has the advantages of small structure, low manufacturing cost, convenience in operation, convenience in carrying and the like.

In the solution, one biological sample membrane can carry a self-luminous object or can carry various self-luminous objects to realize the imaging of the biological sample membrane carrying various self-luminous objects at the same time and to satisfy the scene with higher imaging requirement, thereby greatly improving the practicability of the imaging control apparatus. In this embodiment, through the arrangement of biological membrane placement mechanism, the biological sample membrane can be automatically taken and placed to the surface of the photosensitive chip (or named photoelectric conversion component) in the darkroom, and the surface attachment state of the biological sample membrane can be adjusted in time, for example, the surface attachment state of the biological sample membrane needs to be adjusted to an even and smooth state in time when the surface is uneven due to bubbles thereon, and in the whole process, manual participation is not needed, input cost of labor is reduced, the convenience and the timeliness realized in the imaging control process are improved, the imaging quality and effect on the biological sample membrane are improved when the timeliness, precision and efficiency in the imaging control of the biological sample membrane are ensured, and the application scene with higher imaging requirement is satisfied.

Embodiment 7

An imaging control method for a biological sample membrane according to the embodiment is implemented based on the imaging control apparatus for the biological sample membrane according to Embodiment 5 or 6.

As shown in FIG. 9, an imaging control method for a biological sample membrane according to the embodiment comprises:

S401, sending a first control signal to the biological membrane placement mechanism and controlling the biological membrane placement mechanism to attach the biological sample membrane carrying the self-luminous object to the surface of the photosensitive chip; and S402, sending a second control signal to the biological membrane placement mechanism and controlling the biological membrane placement mechanism to adjust a surface attachment state of the biological sample membrane until a preset placement condition is satisfied.

The photosensitive chip comprises a CMOS chip, a CCD chip, or an amorphous silicon photoelectric conversion detector and the like.

The biological sample membrane comprises a protein membrane, an agarose gel block, an agarose gel strip, a polyacrylamide gel block or a polyacrylamide gel strip and the like. The protein membrane is a protein membrane conventional in the art, and may be, for example, a Western blotting (WB signal) membrane of a protein sample prepared by the method of Embodiment 1.

It should be noted that the implementation principle of the imaging control method of this embodiment is similar to the operation principle of the imaging control apparatus for a biological sample membrane of Embodiment 6, and therefore, the details are not repeated herein.

In this embodiment, through the arrangement of biological membrane placement mechanism, the biological sample membrane can be automatically taken and placed to the surface of the photosensitive chip (or named photoelectric conversion component) in the darkroom, and the surface attachment state of the biological sample membrane can be adjusted in time, for example, the surface attachment state of the biological sample membrane needs to be adjusted to an even and smooth state in time when the surface is uneven due to bubbles thereon, and in the whole process, manual participation is not needed, input cost of labor is reduced, the convenience and the timeliness realized in the imaging control process are improved, the imaging quality and effect on the biological sample membrane are improved when the timeliness, precision and efficiency in the imaging control of the biological sample membrane are ensured, and the application scene with higher imaging requirement is satisfied.

Embodiment 8

An imaging control method for a biological sample membrane according to the embodiment is a further improvement of Embodiment 7, and the improvement is specifically as follows:

In an implementation solution, as shown in FIG. 10, after step S401 and before step S402, the method further comprises:

S40201, acquiring a corresponding first image when the biological sample membrane is attached to the surface of the photosensitive chip;

S40202, analyzing the first image to obtain a corresponding analysis result; and S40203, generating a second control signal when the analysis result indicates that an unevenness state on a surface of the biological sample membrane satisfies the preset placement condition.

In the solution, the image acquisition device is additionally arranged to acquire an image of the attached biological sample membrane in time, so as to determine whether the biological sample membrane is uneven or not in time, and control and adjust the unevenness in time once the unevenness is determined; simultaneously, the image of the attached biological sample membrane after adjustment is acquired in time, then a next adjustment operation is performed according to the analysis result corresponding to the image acquired in real time, and so on until the attachment state of the biological sample membrane reaches the even and smooth state, and in the whole adjustment process, manual participation is also not needed, the cost of labor is reduced and the placement efficiency is improved, the whole operation flow is simplified effectively, imaging control is shortened and time consumption is reduced, in-time and accurate adjustment of the attachment state of the biological sample membrane to an even and smooth state is realized, and subsequent imaging precision is ensured.

In an implementable solution, the imaging control apparatus comprises a driving mechanism electrically connected to the controller, wherein a housing comprises a light shielding cover and a base, one side of the light shielding cover being hinged with one side of the base.

The imaging control method of the embodiment further comprises:

sending a fourth control signal to the driving mechanism to drive the light shielding cover and the base to be closed or separated; and forming the darkroom space inside the housing when the light shielding cover and the base are closed.

In the solution, the light shielding cover of the housing is automatically closed or opened through the driving mechanism, and thus manual participation is not needed, and the whole automation degree and the control efficiency of the control process are ensured.

In an implementable solution, after the darkroom space is formed inside the housing, the imaging control method further comprises:

obtaining a plurality of second images inside the housing within a first set acquisition duration; and performing average value processing on the plurality of second images to obtain a target image.

In the solution, a plurality of second images are obtained and subjected to average value processing to obtain a final target image; compared with a case of acquiring one image, the precision of obtaining an imaging result is effectively improved, the imaging quality is ensured, and a scene required by imaging can be achieved.

In an implementable solution, when the imaging control apparatus further comprises image correction equipment, the imaging control method further comprises:

obtaining, by the photosensitive chip, a first dark field image inside the housing within a second set acquisition duration when the biological sample membrane is not placed in the housing;

obtaining a second dark field image inside the housing within the second set acquisition duration after the biological sample membrane is attached to the surface of the photosensitive chip; and correcting, by the image correction equipment, the second dark field image according to the first dark field image to obtain the target image corresponding to the self-luminous object.

In the solution, the target image of the self-luminous object with higher definition can be effectively and more accurately obtained, and in this process, the operation process is simple, time consumption for imaging is short, and the imaging control apparatus also has the advantages of small structure, low manufacturing cost, convenience in operation, convenience in carrying and the like.

It should be noted that the implementation principle of the imaging control method of this embodiment is similar to the operation principle of the imaging control apparatus for a biological sample membrane of Embodiment 6, and therefore, the details are not repeated herein.

In this embodiment, through the arrangement of biological membrane placement mechanism, the biological sample membrane can be automatically taken and placed to the surface of the photosensitive chip (or named photoelectric conversion component) in the darkroom, and the surface attachment state of the biological sample membrane can be adjusted in time, for example, the surface attachment state of the biological sample membrane needs to be adjusted to an even and smooth state in time when the surface is uneven due to bubbles thereon, and in the whole process, manual participation is not needed, input cost of labor is reduced, the convenience and the timeliness realized in the imaging control process are improved, the imaging quality and effect on the biological sample membrane are improved when the timeliness, precision and efficiency in the imaging control of the biological sample membrane are ensured, and the application scene with higher imaging requirement is satisfied.

Although specific embodiments of the present invention have been described above, it will be understood by those skilled in the art that these embodiments are merely illustrative and that the protection scope of the present invention is defined by the appended claims. Various changes or modifications can be made to these embodiments by those skilled in the art without departing from the principle and spirit of the present invention, and these changes and modifications shall fall within the protection scope of the present invention.

What is claimed is:

1. An imaging control apparatus for a biological sample membrane, comprising a controller, an imaging device and a biological membrane placement mechanism, the imaging device and the biological membrane placement mechanism being communicatively connected to the controller;

wherein the imaging device comprises a housing and a photosensitive chip, a darkroom space is formed inside the housing, and the photosensitive chip is placed in the darkroom space;

the controller is configured for sending a first control signal to the biological membrane placement mechanism and controlling the biological membrane placement mechanism to attach a biological sample membrane carrying a self-luminous object to a surface of the photosensitive chip;

the controller is further configured for sending a second control signal to the biological membrane placement mechanism and controlling the biological membrane placement mechanism to adjust a surface attachment state of the biological sample membrane until a preset placement condition is satisfied;

the imaging control apparatus further comprising one or more cameras communicatively connected to the controller, the one or more cameras being configured for acquiring a corresponding first image when the biological sample membrane is attached to the surface of the photosensitive chip and sending the first image to the controller;

the controller is configured for analyzing the first image to obtain a corresponding analysis result;

the controller is further configured for generating a second control signal when the analysis result indicates that bubbles are present on a surface of the biological sample membrane;

wherein the biological membrane placement mechanism comprises a driving member, a mechanical gripper and a roller structure, the mechanical gripper and the roller structure being electrically connected to the driving member, and the driving member being communicatively connected to the controller;

wherein the roller structure is configured for rolling on the surface of the biological sample membrane to adjust the surface attachment state;

wherein the driving member is configured for controlling the mechanical gripper based on the first control signal to take the biological sample membrane and to attach the biological sample membrane to the surface of the photosensitive chip; and wherein the driving member is further configured for controlling the roller structure to adjust the surface attachment state of the biological sample membrane based on the second control signal to remove the bubbles so as to satisfy the preset placement condition.

2. The imaging control apparatus for a biological sample membrane according to claim 1, wherein the analysis result corresponds to a plurality of bubbles located at areas of the biological sample membrane to be adjusted;

the controller is configured for obtaining position information corresponding to the bubble areas, generating the second control signal according to the position information and sending the second control signal to the driving member;

the driving member is configured for driving the roller structure to perform rolling adjustment on the areas corresponding to the position information in the surface of the biological sample membrane by the second control signal to remove the bubbles so as to satisfy the preset placement condition.

3. The imaging control apparatus for a biological sample membrane according to claim 1, wherein the controller is configured for sending a third control signal to the driving member and controlling the mechanical gripper to take the biological sample membrane attached to the surface of the photosensitive chip out of the housing.

4. The imaging control apparatus for a biological sample membrane according to claim 1, wherein the photosensitive chip is configured for obtaining a plurality of second images inside the housing within a first set acquisition duration after the biological sample membrane is attached to the surface of the photosensitive chip, and sending the plurality of second images to the controller;

the controller is configured for performing average value processing on the plurality of second images to obtain a target image.

5. The imaging control apparatus for a biological sample membrane according to claim 4, wherein a plurality of the biological sample membranes are attached to the photosensitive chip;

when the plurality of biological sample membranes are attached to the photosensitive chip, each sub-image in the target image corresponds to one of the biological sample membranes.

6. The imaging control apparatus for a biological sample membrane according to claim 4, wherein one of the biological sample membranes correspondingly carries a plurality of self-luminous objects, each self-luminous object corresponds to an image acquisition area, and each of the image acquisition area is correspondingly provided with one of the photosensitive chip;

each sub-image in the target image corresponds to one of the image acquisition areas.

7. The imaging control apparatus for a biological sample membrane according to claim 1, wherein the photosensitive chip is configured for obtaining a first dark field image inside the housing within a second set acquisition duration when the biological sample membrane is not placed in the housing;

the photosensitive chip is further configured for obtaining a second dark field image inside the housing within the second set acquisition duration after the biological sample membrane is attached to the surface of the photosensitive chip; and the imaging control apparatus is further configured for correcting the second dark field image according to the first dark field image to obtain a target image corresponding to the self-luminous object.

8. The imaging control apparatus for a biological sample membrane according to claim 7, wherein the photosensitive chip is further configured for obtaining a bright field image inside the housing within the second set acquisition duration when the biological sample membrane is not placed in the housing and light source equipment in the darkroom space is opened;

the imaging control apparatus is further configured for correcting the second dark field image according to the first dark field image and the bright field image to obtain the target image corresponding to the self-luminous object; or the photosensitive chip is further configured for obtaining the corresponding bright field image within the set acquisition duration when the biological sample membrane is not placed in the housing, the housing is in an open state and an external light source provides a uniform light field;

the imaging control apparatus is further configured for correcting the second dark field image according to the first dark field image and the bright field image to obtain the target image corresponding to the self-luminous object.

9. The imaging control apparatus for a biological sample membrane according to claim 8, wherein a corresponding formula to a case that the imaging control apparatus corrects the second dark field image based on the first dark field image and the bright field image to obtain the target image corresponding to the self-luminous object is as follows:

$$I = \frac{I_0 - I_d}{I_f - I_d}$$

5 wherein I represents pixel data corresponding to the target image, $I_0$ represents pixel data corresponding to the second dark field image, $I_d$ represents pixel data corresponding to the first dark field image, and $I_f$ represents pixel data corresponding to the bright field image.

10

\*   \*   \*   \*   \*